(12) United States Patent
Kapur et al.

(10) Patent No.: US 7,766,875 B2
(45) Date of Patent: Aug. 3, 2010

(54) CATHETER FOR REDUCED REFLUX IN TARGETED TISSUE DELIVERY OF A THERAPEUTIC AGENT

(75) Inventors: Terri Kapur, Sharon, MA (US); Daniel Keeley, Boston, MA (US); Greg Schorn, Milford, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 178 days.

(21) Appl. No.: 11/904,724

(22) Filed: Sep. 28, 2007

(65) Prior Publication Data

US 2009/0088695 A1  Apr. 2, 2009

(51) Int. Cl.
*A61M 5/178* (2006.01)
(52) U.S. Cl. .................... 604/164.01; 604/524
(58) Field of Classification Search ............ 604/164.01, 604/523, 525
See application file for complete search history.

(56) References Cited

U.S. PATENT DOCUMENTS

| | | | |
|---|---|---|---|
| 3,713,447 A | 1/1973 | Adair | |
| 4,547,194 A | 10/1985 | Moorehead | |
| 4,559,046 A | 12/1985 | Groshong et al. | |
| 4,787,882 A * | 11/1988 | Claren | 604/6.16 |
| 4,995,868 A | 2/1991 | Brazier | |
| 5,462,523 A | 10/1995 | Samson et al. | |
| 5,643,226 A * | 7/1997 | Cosgrove et al. | 604/264 |
| 5,693,030 A | 12/1997 | Lee et al. | |
| 5,720,720 A | 2/1998 | Laske et al. | |
| 5,749,826 A | 5/1998 | Faulkner | |
| 5,895,378 A | 4/1999 | Nita | |
| 5,931,831 A * | 8/1999 | Linder | 604/523 |
| 5,984,908 A * | 11/1999 | Davis et al. | 604/524 |
| 5,993,473 A * | 11/1999 | Chan et al. | 606/192 |
| 6,094,598 A | 7/2000 | Elsberry et al. | |
| 6,110,155 A | 8/2000 | Baudino | |
| 6,183,462 B1 | 2/2001 | Beals | |
| 6,210,346 B1 | 4/2001 | Hall et al. | |
| 6,358,229 B1 | 3/2002 | Tihon | |
| 6,428,498 B2 | 8/2002 | Uflacker | |
| 6,456,886 B1 | 9/2002 | Howard, III et al. | |
| 6,497,699 B1 | 12/2002 | Ludvig et al. | |
| 6,524,296 B1 | 2/2003 | Beals | |
| 6,602,241 B2 | 8/2003 | Makower et al. | |
| 6,749,583 B2 * | 6/2004 | Briscoe et al. | 604/96.01 |

(Continued)

FOREIGN PATENT DOCUMENTS

WO  WO 01/28619  4/2001

(Continued)

*Primary Examiner*—Nicholas D Lucchesi
*Assistant Examiner*—Gerald Landry, II
(74) *Attorney, Agent, or Firm*—Cheryl F. Cohen, LLC

(57) ABSTRACT

A catheter for delivery of a therapeutic agent directly into a targeted tissue that reduces or substantially prevents reflux and back flow by providing rigidity and strength via a stylet thereby eliminating the need for a guide or delivery sheath during positioning. The catheter has a flexible proximal section and a substantially rigid distal section formed from a plurality of distal subsections. The proximal and distal sections having decreasing outer diameters starting from the proximal end and advancing towards the distal end. The distal subsection closest to the distal end providing an adjustable flow rate via multiple output ports defined radially therein while the distal end itself is closed off.

23 Claims, 2 Drawing Sheets

U.S. PATENT DOCUMENTS

| | | |
|---|---|---|
| 6,768,425 B2 | 7/2004 | Flaherty et al. |
| 6,951,555 B1 | 10/2005 | Suresh et al. |
| 7,069,634 B1 | 7/2006 | Elsberry |
| 7,108,680 B2 | 9/2006 | Rohr et al. |
| 7,335,187 B2 * | 2/2008 | Altman .................. 604/164.08 |
| 2001/0021840 A1 | 9/2001 | Suresh et al. |
| 2001/0025169 A1 | 9/2001 | Kaneshige |
| 2002/0177866 A1 | 11/2002 | Weikel et al. |
| 2005/0154297 A1 | 7/2005 | Gill |
| 2006/0094983 A1 * | 5/2006 | Burbank et al. ............. 600/567 |
| 2006/0135945 A1 | 6/2006 | Bankiewicz et al. |
| 2007/0078386 A1 | 4/2007 | Salazar |
| 2007/0088295 A1 | 4/2007 | Bankiewicz |
| 2007/0112302 A1 | 5/2007 | Yu |

FOREIGN PATENT DOCUMENTS

| | | |
|---|---|---|
| WO | WO 02/00286 | 1/2002 |

* cited by examiner

CATHETER FOR REDUCED REFLUX IN TARGETED TISSUE DELIVERY OF A THERAPEUTIC AGENT

BACKGROUND OF THE INVENTION

1. Field of the Invention

The present invention is directed to a catheter for drug delivery and, in particular, to a catheter for the delivery of a therapeutic agent into body tissue while reducing unwanted reflux.

2. Description of Related Art

Fluids or therapeutic agents may be delivered into various parts of the body that already contain a fluid or liquid such as epidurally or intrathecally into the spinal space. The delivery of a therapeutic agent into a fluid or liquid does not produce as much resistance or pressure as when dispensing directly into tissue. The fluid being dispensed from the catheter attempts to find the path of least pressure or resistance. In the case of tissue as the target of injection this path of least resistance or pressure often times causes the therapeutic agent to disadvantageously travel back up the catheter track defined as the space between the targeted tissue and outer surface of the catheter, otherwise referred to as reflux, back flow or leakage. Such back flow may result in catheter contamination or exposure of a larger area of the tissue to the therapeutic agent.

Convection enhanced delivery is the injection under positive pressure of fluid containing a therapeutic agent. This technology allows focused delivery of a therapeutic agent to a specific target area. Direct delivery is advantageous in that it reduces if not eliminates side effect complications that would otherwise arise from the delivery of a the therapeutic agent systemically. Another advantage is that convection enhanced delivery can increase the activity of the drug and deliver therapeutic concentrations not possible using conventional means. Therapeutic agents previously unable to reach a targeted tissue through oral delivery may now be reconsidered for direct delivery.

In brain tissue, drug formulations are difficult to develop due to the blood-brain barrier transport properties. Typically, molecules enter the cerebral spinal fluid or brain tissue in three ways: (i) by diffusion of lipid-soluble substances, (ii) by facilitative and energy-dependent receptor-mediated transport of specific water-soluble substances, and (iii) by ion channels. Protein based drugs do not typically fall into any of these three categories, and thus are usually not amenable to oral or intravenous delivery.

Recent study has focused on the direct infusion of proteins in the brain as a possible treatment of Parkinson's disease. In particular, the treatment of Parkinson's disease has recently concentrated on the delivery of the therapeutic agent directly into the grey matter brain tissue such as in the putamen. Conventional catheters permit backflow and reflux back up the catheter track that produces undesirable side effects if used to deliver proteins to the putamen.

U.S. Patent Publication No. 2007/0088295 discloses a step-design cannula and delivery system for chronic delivery of therapeutic substances into the brain using convention-enhanced delivery of therapeutic substances and which effectively prevents reflux in vivo and maximizes distribution into the brain. A delivery sheath is used for positioning the infusion cannula in the brain. The proximal end of the delivery sheath functions as the most external segment of the step-design of the infusion cannula, thereby increasing the overall number of steps in the step-design. Once the delivery sheath and cannula are placed at the proper depth, the assembly is fixed in position, for example, using an o-ring shaped holding bracket through which a bone screw is inserted to rigidly attach the holding bracket to the skull. After the assembly is positioned, only the upper portion of the delivery sheath is removed by cutting the sheath just above the points where the infusion cannula bends over leaving in place that portion of the delivery sheath implanted in the body. The system in accordance with the published patent application employs a delivery sheath as a guide because the central lumen is populated from the source to the distal tip with an infusion tube and thus a stylet cannot be directly inserted into the central lumen. The use of a delivery sheath while positioning the cannula in such a manner and leaving it implanted thereafter is disadvantageous in that it provides an allowance or opening between the proximal end of the delivery sheath and the distal catheter that is prone to reflux and back flow of the therapeutic substance thereby defeating the underlying purpose of the device. In addition, the published patented application catheter has a single exit port through the distal end of the catheter.

It is therefore desirable to develop an improved catheter design for delivery of a therapeutic agent directly into tissue that reduces or prevents reflux and back flow while eliminating the need for a guide or delivery sheath during positioning. Furthermore, an improved catheter is needed with an adjustable flow rate via multiple output ports.

SUMMARY OF THE INVENTION

The present invention relates to a catheter for delivery of a therapeutic agent directly into a targeted tissue that reduces or substantially prevents reflux and back flow by providing rigidity and strength via a stylet thereby eliminating the need for a guide or delivery sheath during positioning. The catheter has a flexible proximal section and a substantially rigid distal section formed from a plurality of distal subsections. The proximal and distal subsections having decreasing outer diameters starting from the proximal end and advancing towards the distal end. The distal subsection closest to the distal end providing an adjustable flow rate via multiple output ports defined radially therein while the distal end itself is closed off.

Another aspect of the present invention is directed to a catheter having a proximal end and an opposite closed off distal end. In accordance with the present invention, the catheter further includes a proximal section disposed closest to the proximal end, wherein the proximal section has a substantially uniform outer diameter and is formed of a flexible material. Furthermore, the catheter also includes a distal section disposed closest to the distal end and formed of a substantially rigid material. The distal section is formed by a plurality of distal subsections including at least a first distal subsection closest to the proximal end and having a substantially uniform outer diameter and a second distal subsection closest to the distal end and having a substantially uniform outer diameter, wherein the outer diameter of the first distal subsection is greater than the outer diameter of the second distal subsection. It is the second distal subsection in which a plurality of openings are defined radially therein. A lumen is defined therethrough the proximal and distal sections extending from the proximal end to the distal end.

Still another aspect of the present invention is directed to a method for positioning the catheter as described in the preceding paragraph. Initially, a stylet is inserted into the lumen, the stylet extending in the lumen at least partially in the distal section. The assembled stylet and catheter are then positioned at the targeted tissue. After being properly positioned, the stylet is completely removed while leaving in place the positioned catheter. In accordance with the present invention, the use of a stylet eliminates the need for a delivery sheath so that the hole formed in the tissue by the catheter is limited in size to substantially the largest outer diameter in the distal section. It is the stylet that provides all necessary rigidity over the entire length of the catheter during insertion so that it may be properly positioned proximate the targeted tissue site

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

Figure 1:
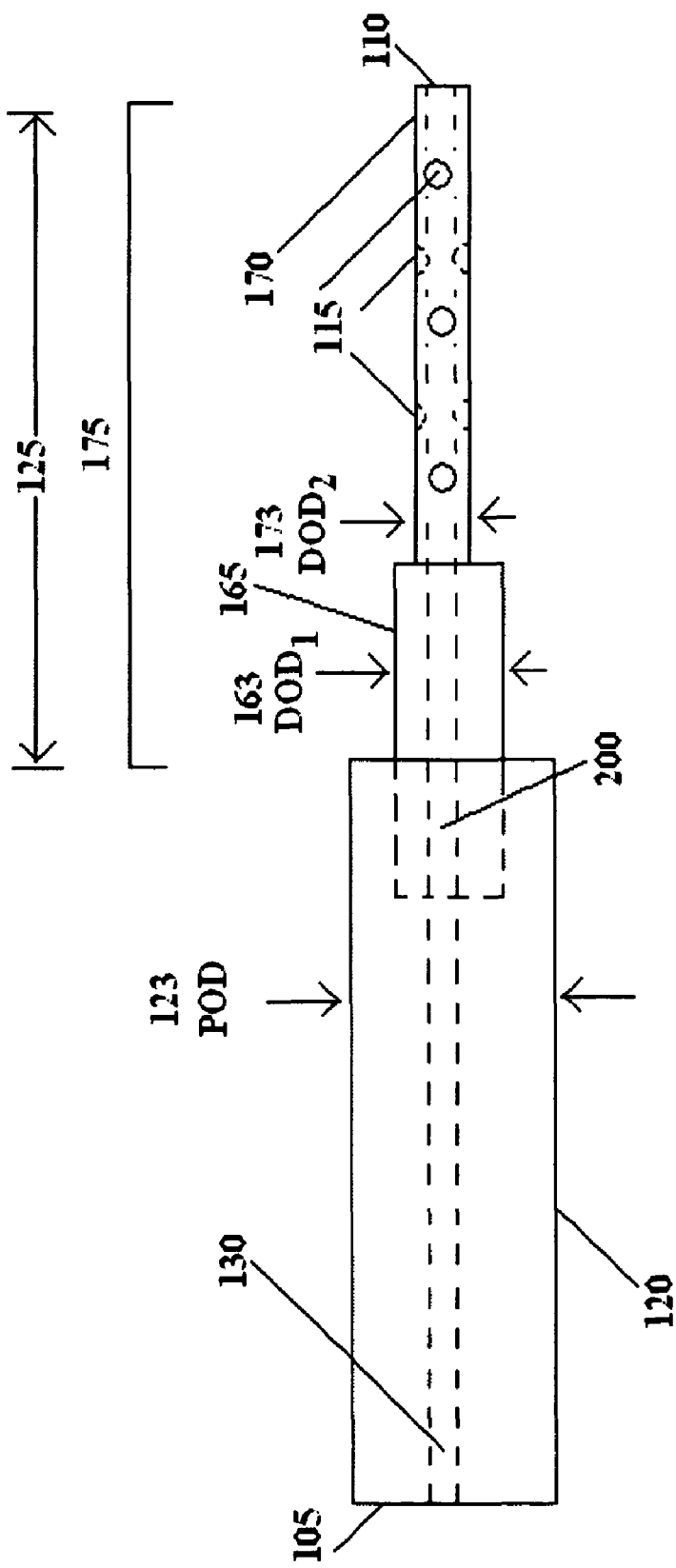
FIG. 1 depicts an exemplary schematic diagram of a catheter for reducing reflux during direct injection into targeted tissue in accordance with the present invention.

FIG. 1 shows a catheter 100 in accordance with the present invention for delivery of a therapeutic agent, medicine, drug or other fluid directly into a targeted tissue. The specific geometry of the catheter reduces or substantially prevents reflux, leakage and back flow while eliminating the need for a guide or delivery sheath during positioning.

Catheter 100 has a proximal end or tip 105 and an opposite closed distal end or tip 110. Referring to FIG. 1, catheter 100 is formed by a plurality of stepped sections having different size diameters including a proximal section 120 closest to the proximal end 105 and a distal section 175 closest to the distal end 110, wherein the distal section 175 is itself formed by a plurality of distal subsections 165, 170. Starting from the proximal end 105 and advancing towards the distal end 110, each distal subsection has an outer diameter smaller than the previous distal subsection.

Proximal section 120 is preferably formed of a flexible material (e.g., silicone or polyurethane) whereas distal section 175 (including distal subsections 165, 170) is preferably formed of a substantially rigid material such as stainless steel, titanium, polyetherimide (PEI) or polyetheretherketone (PEEK). In a preferred embodiment, the length 125 of the distal section 175, is between approximately 1.0 cm to approximately 4.0 cm when used to deliver a therapeutic agent to the putamen. It is contemplated and within the intended scope of the present invention to vary the length of the distal section 175, as desired, depending on the size and depth of the targeted tissue into which the catheter is to be inserted.

The catheter 100 has a lumen or passageway 130 extending from the proximal end 105 to the distal end 110. Proximal section 120 of the catheter has a substantially uniform outer diameter (POD) 123. At the opposite end of the catheter 100, the distal section 175 has a non-uniform or stepped outer diameter. Specifically, the distal section 175 comprises two different outer diameter subsections. Starting at the proximal end and advancing towards the distal end, the outer diameter of each distal subsection in the distal section 175 is smaller than the outer diameter of the previous distal subsection with the distal subsection having the smallest outer diameter being proximate the sealed distal end 110. In addition, the, outer diameter of the distal subsection 165 closest to the proximal section 120 has an outer diameter $DOD_1$ 163 that is smaller than the outer diameter POD 123 of the proximal section 120.

Referring to the exemplary embodiment shown, in FIG. 1, the distal section 175 includes two different outer diameter distal subsections, namely, a first distal subsection having an outer diameter ($DOD_1$) 163 and a second distal subsection having an outer diameter ($DOD_2$) 173, wherein $DOD_1$ 163 is greater than $DOD_2$ 173. Any number of two or more different outer diameter distal subsections may form the distal section 175 so long as the outer diameters decrease in size starting from the proximal end and advancing towards the distal end.

The distal end 110 of the catheter 100 is closed off or sealed and any number of one or more ports or openings 115, preferably between approximately 2 and approximately 50 openings, are defined radially therethrough the outer perimeter in the distal subsection 170. Each port or opening 115 may be any diameter, as desired. In a preferred embodiment, the diameter of each opening 115 is in the range between approximately 0.01 mm and approximately 4 mm. It is noted that the openings 115 shown in FIG. 1 are all substantially equal in diameter, however, the diameter of all of the openings need not be uniform. Furthermore, in the illustrative example shown in FIG. 1 the openings 115 are arranged or disposed substantially symmetrically about the outer perimeter of the distal subsection 170 of the catheter to permit substantially uniform delivery of the therapeutic agent in all directions. Alternatively, the arrangement or positioning of the openings 115 defined in the outer perimeter of the distal subsection 170 of the catheter may be asymmetric or altered in any desired configuration. Openings 115 are disposed only in the distal subsection 170 closest to the distal end 110, that is, the distal subsection having the smallest outer diameter in the distal segment 175. In a preferred embodiment, optimal delivery is achieved when factors such as the number of distal subsections in the distal section 175, the number of openings or ports 115, and the diameter size and arrangement of such openings are selected so that the flux of all ports or openings 115 is maintained preferably between approximately 0.500 ($\mu$l/min)/mm$^2$ and approximately 1.000 ($\mu$l/min)/mm$^2$.

Figure 2:
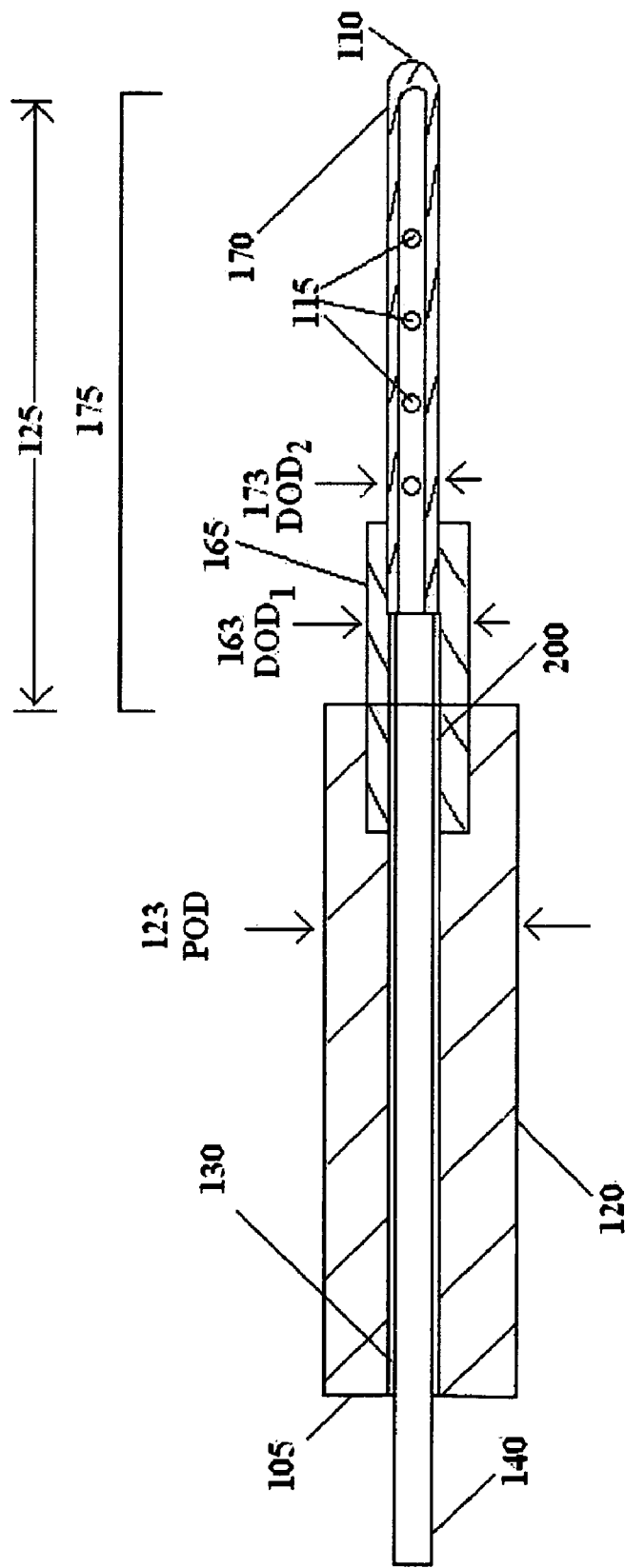
FIG. 2 shows a cross-section view of the assembled catheter and stylet in accordance with the present invention.

FIG. 2 shows the assembled catheter 100 of FIG. 1 and interlocking stylet 140 received through its lumen 130. To allow for insertion, the stylet 140 has an outer diameter that is less than the inner diameter of the lumen 130. When using a conventional stylet having an outer diameter of approximately 0.45 mm, the lumen 130 has an inner diameter preferably of approximately 0.6 mm. The distal tip of stylet 140 extends at least partially into the portion of the lumen 200 disposed in distal subsection 165. It is contemplated and within the intended scope of the present invention for the distal tip of stylet 140 to extend at least partially into the lumen 130 extending through more than one distal subsection and may be disposed substantially to the distal end or tip 110 of the catheter 100. As a result of such configuration, the stylet 140 within lumen 200 of distal section 165 provides the necessary rigidity or strengthening over the entire length of the catheter 100 during insertion so that it may be properly positioned proximate the targeted tissue site. Once properly positioned, the stylet 140 is removed leaving the flexible proximal section 120 of the catheter 100 in place. The use of a stylet or guidewire disposed within the lumen 130 eliminates the need for a permanently affixed delivery sheath that would disadvantageously enlarge the opening around the outer diameter of the distal end of the catheter and thereby creates a larger allowance prone to reflux, back flow or leakage. After the catheter 100 is positioned in place and the stylet 140 is removed, proximal end 105 is attached to a pump catheter, which is tunneled subcutaneously to the implanted pump. The infusate is then dispensed through lumen 130 to the outlet ports 115 and into the targeted tissue.

The catheter in accordance with the present invention is suitable for use with the delivery of a therapeutic agent or fluid directly into a targeted tissue. One example of such application is for the treatment of brain cancer or Parkinson's disease, wherein the delivery of infusate is directly to the grey matter tissue or specifically the putamen. Some additional possible uses may be found in the treatment of obesity, depression, stroke, epilepsy, or other movement disorders. Other alternative uses may include the targeted treatment of tumors elsewhere in the body such as the liver or spinal cord, the delivery of angiogenic factors to sick or dying deep tissue, such as in muscle, the delivery of nutrients or growth factors to places where capillary damage has prevented adequate delivery of nutrients or healing factors. Still other alternative uses are contemplated and within the intended scope of the present invention.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A catheter having a proximal end and an opposite closed off distal end, the catheter comprising:
   a proximal section disposed closest to the proximal end, the proximal section having a substantially uniform outer diameter, the proximal section being formed of a flexible material;
   a distal section disposed closest to the distal end; the distal section being formed of a substantially rigid material; the distal section formed by a plurality of distal subsections including at least a first distal subsection closest to the proximal end and having a substantially uniform outer diameter and a second distal subsection closest to the distal end and having a substantially uniform outer diameter, wherein the outer diameter of the first distal subsection is greater than the outer diameter of the second distal subsection; the second distal subsection having a plurality of openings defined radially therein; and
   the proximal and distal sections having a lumen defined therethrough extending from the proximal end to the distal end;
   wherein the second distal section overlaps with the first distal section, but the second distal section does not overlap with the proximal section.

2. The catheter in accordance with claim 1, wherein starting from the proximal end and advancing towards the distal end, each of the plural distal subsections has an outer diameter smaller than the previous distal subsection.

3. The catheter in accordance with claim 2, wherein the outer diameter of the first distal subsection is smaller than the outer diameter of the proximal section.

4. The catheter in accordance with claim 1, wherein the plural openings are only defined in the second distal subsection.

5. The catheter in accordance with claim 1, wherein the lumen is configured to receive a stylet therein so as to eliminate the need for a delivery sheath.

6. The catheter in accordance with claim 5, wherein the lumen has an inner diameter of approximately 0.6 mm.

7. The catheter in accordance with claim 6, wherein the lumen is configured to permit passage of a stylet at least partially into the distal section.

8. The catheter in accordance with claim 7, wherein the lumen is configured to permit passage of a stylet substantially to the distal end.

9. The catheter in accordance with claim 1, wherein the lumen delivers infusate to a targeted tissue.

10. The catheter in accordance with claim 1, wherein the distal section is made of stainless steel.

11. The catheter in accordance with claim 1, wherein the distal section is made of titanium.

12. The catheter in accordance with claim 1, wherein the distal section has a length between approximately 1.0 cm to approximately 4.0 cm.

13. The catheter in accordance with claim 1, wherein the proximal section is made of silicone.

14. The catheter in accordance with claim 1, wherein the proximal section is made of polyurethane.

15. The catheter in accordance with claim 1, wherein the distal section is configured to receive a stylet at least partially in the lumen.

16. The catheter in accordance with claim 15, wherein the distal section is configured to receive a stylet in the lumen extending substantially to the distal end.

17. A method for positioning of a catheter to deliver a therapeutic agent to a targeted tissue, the catheter having a proximal end and an opposite closed off distal end; the catheter further comprising a proximal section disposed closest to the proximal end, the proximal section having a substantially uniform outer diameter, the proximal section being formed of a flexible material; the catheter also including a distal section disposed closest to the distal end; the distal section being formed of a substantially rigid material; the distal section formed by a plurality of distal subsections including at least a first distal subsection closest to the proximal end and having a substantially uniform outer diameter and a second distal subsection closest to the distal end and having a substantially uniform outer diameter, wherein the outer diameter of the first distal subsection is greater than the outer diameter of the second distal subsection; the second distal subsection having a plurality of openings defined radially therein; and the proximal and distal sections having a lumen defined therethrough extending from the proximal end to the distal end, comprising the steps of:
   inserting a stylet into the lumen, the stylet extending into the lumen at least partially in the distal section;
   wherein the second distal section overlaps with the first distal section, but the second distal section does not overlap with the proximal section.

18. The method in accordance with claim 17, further comprising the step of positioning the assembled stylet and catheter at the targeted tissue.

19. The method in accordance with claim 18, further comprising the step of removing the stylet completely while leaving in place the positioned catheter.

20. The method in accordance with claim 17, wherein the stylet eliminates the need for a delivery sheath.

21. The method in accordance with claim 19, wherein once positioned, a hole formed in the targeted tissue by the catheter is limited in size to substantially the largest outer diameter in the distal section.

22. The method in accordance with claim 17, wherein the stylet provides all necessary rigidity over the entire length of the catheter during insertion so that it may be properly positioned proximate the targeted tissue site.

23. The method in accordance with claim 17, wherein the inserting step comprises inserting the stylet into the lumen defined in the distal section so that it extends substantially to the distal end.

* * * * *